(12) United States Patent
Inoue et al.

(10) Patent No.: US 6,670,499 B1
(45) Date of Patent: Dec. 30, 2003

(54) ADAMANTANE DERIVATIVES AND PROCESSES FOR THE PREPARATION THEREOF

(75) Inventors: Keizo Inoue, Himeji (JP); Shinya Nagano, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 557 days.

(21) Appl. No.: 09/869,858

(22) PCT Filed: Nov. 7, 2000

(86) PCT No.: PCT/JP00/07810

§ 371 (c)(1),
(2), (4) Date: Jul. 6, 2001

(87) PCT Pub. No.: WO01/34556

PCT Pub. Date: May 17, 2001

(30) Foreign Application Priority Data

Nov. 8, 1999 (JP) ............................................. 11-317536
Nov. 8, 1999 (JP) ............................................. 11-317537
Nov. 8, 1999 (JP) ............................................. 11-317538

(51) Int. Cl.⁷ ............................................... C07C 69/74
(52) U.S. Cl. ........................ 560/117; 560/128; 560/129; 560/157; 560/205

(58) Field of Search ................................. 560/205, 128, 560/129, 157, 117

(56) References Cited

FOREIGN PATENT DOCUMENTS

| EP | 0915077 A1 | * 11/1998 |
| EP | A 10915077 | 5/1999 |
| JP | A 63-233907 | 9/1988 |
| JP | 63-233907 | * 9/1988 |

* cited by examiner

Primary Examiner—Paul J. Killos
Assistant Examiner—Héctor M. Reyes
(74) Attorney, Agent, or Firm—Birch, Stewart, Kolasch & Birch, LLP

(57) ABSTRACT

Adamantane derivatives in which two (meth)acryloyloxyalkyl groups are bonded with an adamantane ring through ester groups, adamantane derivatives in which two adamantane rings are bonded through an alkylene group and two urethane bonds, which two adamantane rings each have a (meth)acryloyloxy group bonded thereto directly or through a coupling group, and adamantane derivatives each having a structure in which a group containing an adamantane ring hangs on the alkylene group of an alkylene glycol di(meth)acrylate. The compounds are useful as dental materials intermediates therefor, and as intermediates for optical materials such as lenses.

5 Claims, No Drawings

ADAMANTANE DERIVATIVES AND PROCESSES FOR THE PREPARATION THEREOF

This application is the national phase under 35 U.S.C. §371 of PCT International Application No. PCT/JP00/07810 which has an International filing date of Nov. 7, 2000, which designated the United States of America and was not published in English.

TECHNICAL FIELD

The present invention relates to novel adamantane derivatives which are useful, for example, as dental materials or raw materials therefor, and as raw materials for optical materials such as lenses.

BACKGROUND ART

Adamantane compounds have a variety of functions due to their special non-aromatic and rigid ring structures and receive attention in various areas.

For example, proposes have been made to use polymerizable monomers each having an adamantane skeleton or polymers thereof as dental materials. Such dental materials include, for example, cementing materials for setting inlays, crowns and other teeth crown materials to cavities or abutments, bonding materials for bonding with tooth or restorative dental materials to thereby hold the restorative dental materials, filling materials for packing or filling the socket of a tooth, and surface lubricants.

Japanese Unexamined Patent Application Publication No. 63-233906 discloses a dental material containing an acrylic polymer comprising, as a monomer, a (meth)acrylic ester of an alcohol having an adamantane skeleton. Japanese Unexamined Patent Application Publication No. 63-233907 discloses a dental material containing a urethane derivative of adamantane. Japanese Unexamined Patent Application Publication No. 4-80223 and Japanese Unexamined Patent Application Publication No. 4-360809 each disclose a dental surface lubricant containing a polymerizable urethane compound having an adamantane skeleton, a volatile compound, and a polymerization initiator.

However, these dental materials are not always satisfactory in, for example, water resistance, stability and luster.

DISCLOSURE OF INVENTION

Accordingly, an object of the present invention is to provide novel adamantane derivatives which are useful as, for example, raw materials for dental materials.

After intensive investigations to achieve the above objects, the present inventors have found novel adamantane derivatives in which two (meth)acryloyloxyalkyl groups are bonded with an adamantane ring through ester groups, novel adamantane derivatives in which two adamantane rings are bonded through an alkylene group and two urethane bonds, which two adamantane rings each have a (meth)acryloyloxy group bonded thereto directly or through a coupling group, and novel adamantane derivatives each having a structure in which a group containing an adamantane ring hangs on the alkylene group of an alkylene glycol di(meth)acrylate. The present invention has been accomplished based on these findings.

Specifically, the present invention provides, in an aspect, an adamantane derivative represented by the following Formula (1), (6) or (9):

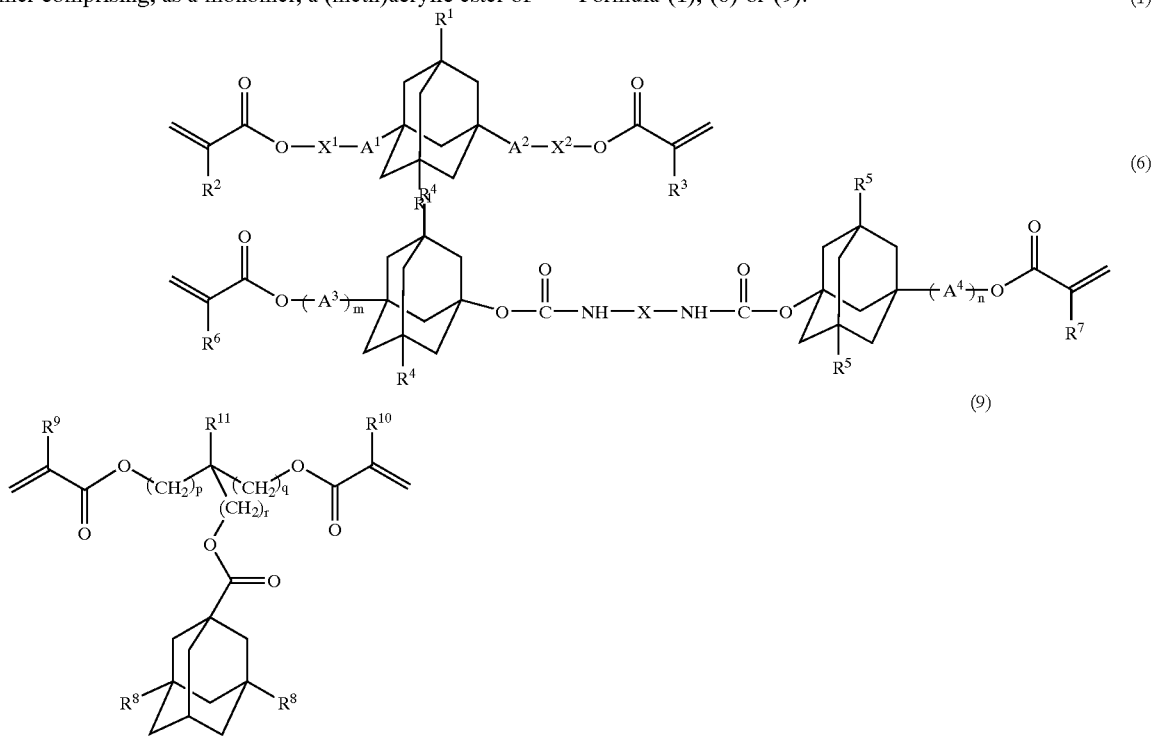

[wherein, in Formula (1), $R^1$ is a hydrogen atom or a methyl group; each of $R^2$ and $R^3$ is, identical to or different from each other, a hydrogen atom or a methyl group; each of $A^1$ and $A^2$ is, identical to or different from each other, a —C(=O)—O— group or —O—C (=O)— group, where the right-hand sides of these two groups are on the adamantane ring side; each of $X^1$ and $X^2$ is, identical to or different from each other, a straight- or branched-chain alkylene group having from 1 to 12 carbon atoms, in Formula (6), each of $R^4$ and $R^5$ is, identical to or different from each other, a hydrogen atom or a methyl group; each of $R^6$ and $R^7$ is, identical to or different from each other, a hydrogen atom or a methyl group; each of $A^3$ and $A^4$ is, identical to or different from each other, a group represented by the following formula:

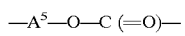

(wherein $A^5$ is a straight- or branched-chain alkylene group having from 1 to 6 carbon atoms, where the right-hand side of the above formula is on the adamantane ring side); X is a straight- or branched-chain alkylene group having from 1 to 12 carbon atoms; and each of m and n denotes 0 or 1, in Formula (9), $R^8$ is a hydrogen atom or a methyl group; each of $R^9$ and $R^{10}$ is, identical to or different from each other, a hydrogen atom or a methyl group; $R^{11}$ is a hydrogen atom, a straight- or branched-chain alkyl group having from 1 to 4 carbon atoms, or a group represented by the following Formula (10):

—(CH$_2$)$_s$—O—R$^{12}$          (10)

(wherein $R^{12}$ is an acryloyl group, a methacryloyl group, an 1-adamantylcarbonyl group or a 3,5-dimethyladamant-1-ylcarbonyl group; and s denotes an integer from 1 to 6); and each of p, q and r denotes an integer from 1 to 6].

In another aspect, the present invention provides a process for producing an adamantane derivative (hereinafter briefly referred to as "Production Process 1"), which process includes the step of allowing an adamantanedicarboxylic acid represented by the following Formula (2) or a reactive derivative thereof:

(2)

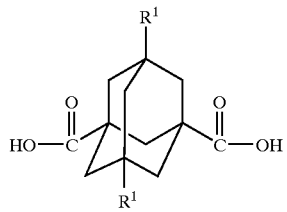

(wherein $R^1$ is a hydrogen atom or a methyl group) to react with (meth)acrylic hydroxyalkyl esters represented by the following Formulae (3a) and (3b):

(3a)

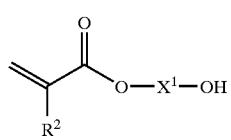

(3b)

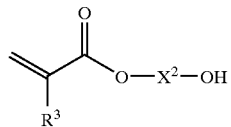

(wherein each of $R^2$ and $R^3$ is, identical to or different from each other, a hydrogen atom or a methyl group; and each of $X^1$ and $X^2$ is, identical to or different from each other, a straight- or branched-chain alkylene group having from 1 to 12 carbon atoms)

to thereby yield an adamantane derivative represented by the following Formula (1a):

(1a)

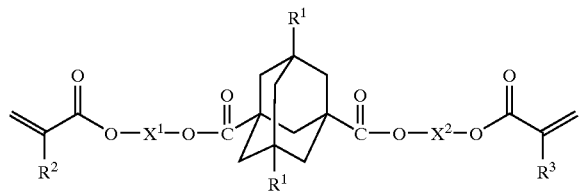

(wherein $R^1$, $R^2$, $R^3$, $X^1$ and $X^2$ have the same meanings as defined above).

In a further aspect, the present invention provides a process for producing an adamantane derivative (hereinafter briefly referred to as "Production Process 2"), which process includes the step of allowing an adamantanediol represented by the following Formula (4):

(4)

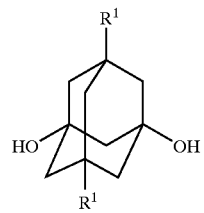

(wherein $R^1$ is a hydrogen atom or a methyl group) to react with (meth)acryloyloxy-group-containing carboxylic acids represented by the following Formulae (5a) and (5b) or reactive derivatives thereof:

(5a)

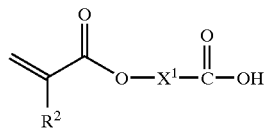

(5b)

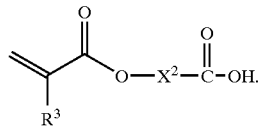

(wherein each of $R^2$ and $R^3$ is, identical to or different from each other, a hydrogen atom or a methyl group; and each of $X^1$ and $X^2$ is, identical to or different from each other, a straight- or branched-chain alkylene group having from 1 to 12 carbon atoms)

to thereby yield an adamantane derivative represented by the following Formula (1b):

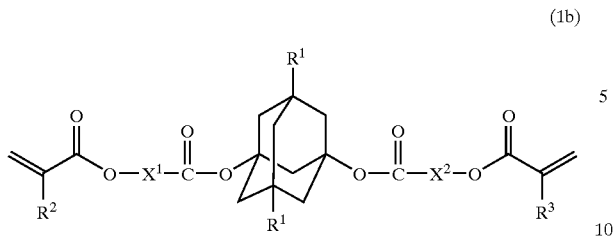
(1b)

(wherein $R^1$, $R^2$, $R^3$, $X^1$ and $X^2$ have the same meanings as defined above).

The present invention provides, in still another aspect, a process for producing an adamantane derivative, which process includes the step of allowing adamantanol derivatives represented by the following Formulae (7a) and (7b):

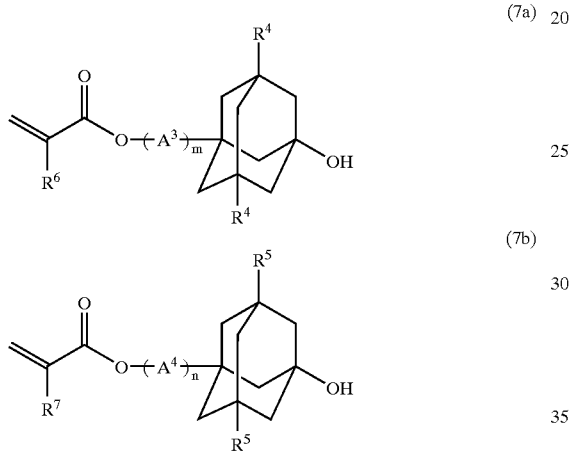
(7a)

(7b)

[wherein each of $R^4$ and $R^5$ is, identical to or different from each other, a hydrogen atom or a methyl group; each of $R^6$ and $R^7$ is, identical to or different from each other, a hydrogen atom or a methyl group; each of $A^3$ and $A^4$ is, identical to or different from each other, a group represented by the following formula:

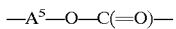
—$A^5$—O—C(=O)—

(wherein $A^5$ is a straight- or branched-chain alkylene group having from 1 to 6 carbon atoms, where the right-hand side of the above formula is on the adamantane ring side); and each of m and n independently denotes 0 or 1]
to react with a diisocyanate compound represented by the following Formula (8):

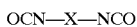
OCN—X—NCO (8)

(wherein X is a straight- or branched-chain alkylene group having from 1 to 12 carbon atoms)
to thereby yield the adamantane derivative represented by Formula (6).

In addition and advantageously, the present invention provides a process for producing an adamantane derivative, which process includes the step of allowing an adamantanecarboxylic acid represented by the following Formula (11) or a reactive derivative thereof:

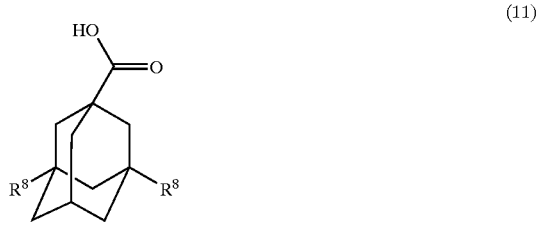
(11)

(wherein $R^8$ is a hydrogen atom or a methyl group) to react with a compound represented by the following Formula (12):

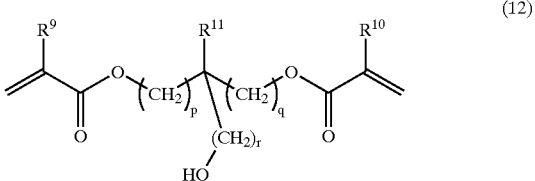
(12)

[wherein each of $R^9$ and $R^{10}$ is, identical to or different from each other, a hydrogen atom or a methyl group; $R^{11}$ is a hydrogen atom, a straight- or branched-chain alkyl group having from 1 to 4 carbon atoms, or a group represented by Formula (10); and
each of p, q and r independently denotes an integer from 1 to 6]
to thereby yield the adamantane derivative represented by Formula (9).

In the present description, the terms "acrylic" and "methacrylic" may be generically referred to as "(meth)acrylic", and the terms "acryloyl" and "methacryloyl" may be generically referred to as "(meth)acryloyl".

Best Mode for Carrying Out the Invention
[Adamantane Derivatives Represented by Formula (1)]

In the adamantane derivatives of the present invention represented by Formula (1), each of $X^1$ and $X^2$ is, identical to or different from each other, a straight- or branched-chain alkylene group having from 1 to 12 carbon atoms.

Such straight- or branched-chain alkylene groups each having from 1 to 12 carbon atoms include, for example, ethylene, ethylene, methylethylene, trimethylene, 1-methyltrimethylene, 2-methyltrimethylene, 2,2-dimethyltrimethylene, tetramethylene, pentamethylene, hexamethylene, heptamethylene, octamethylene, nonamethylene, 2,2,4-trimethylhexamethylene, decamethylene, and dodecamethylene groups. Among them, straight- or branched-chain alkylene groups each having from about 2 to about 8 carbon atoms are preferred, of which straight- or branched-chain alkylene groups each having from about 2 to about 6 carbon atoms are typically preferred.

Illustrative compounds represented by Formula (1) include, but are not limited to,
bis[2-(meth)acryloyloxyethyl]1,3-adamantanedicarboxylate,
bis[2-(meth)acryloyloxyethyl]5,7-dimethyl-1,3-adamantanedicarboxylate,
bis[3-(meth)acryloyloxypropyl]1,3-adamantanedicarboxylate,
bis[3-(meth)acryloyloxypropyl]5,7-dimethyl-1,3-adamantanedicarboxylate,
bis[2-(meth)acryloyloxy-1-methylethyl]1,3-adamantanedicarboxylate, bis[2-(meth)acryloyloxy-1-methylethyl]5,7-dimethyl-1,3-adamantanedicarboxylate,
bis[2-(meth)acryloyloxy-2-methylethyl]1,3-adamantanedicarboxylate,
bis[2-(meth)acryloyloxy-2-methylethyl]5,7-dimethyl-1,3-adamantanedicarboxylate,
bis[4-(meth)acryloyloxybutyl]1,3-adamantanedicarboxylate,
bis[4-(meth)acryloyloxybutyl]5,7-dimethyl-1,3-adamantanedicarboxylate,
bis[3-(meth)acryloyloxy-2-methylpropyl]1,3-adamantanedicarboxylate,
bis[3-(meth)acryloyloxy-2-methylpropyl]5,7-dimethyl-1,3-adamantanedicarboxylate,
bis[5-(meth)acryloyloxypentyl]1,3-adamantanedicarboxylate,
bis[5-(meth)acryloyloxypentyl]5,7-dimethyl-1,3-adamantanedicarboxylate,
bis[3-(meth)acryloyloxy-2,2-dimethylpropyl]1,3-adamantanedicarboxylate,
bis[3-(meth)acryloyloxy-2,2-dimethylpropyl]5,7-dimethyl-1,3-adamantanedicarboxylate,
bis[6-(meth)acryloyloxyhexyl]1,3-adamantanedicarboxylate,
bis[6-(meth)acryloyloxyhexyl]5,7-dimethyl-1,3-adamantanedicarboxylate, and other compounds in which $A^1$ and $A^2$ are both —O—C(=O)— groups (the right-hand sides of the groups are on the adamantane ring side);
1,3-bis[2-(meth)acryloyloxyethylcarbonyloxy]adamantane,
5,7-dimethyl-1,3-bis[2-(meth)acryloyloxyethylcarbonyloxy]adamantane,
1,3-bis[3-(meth)acryloyloxypropylcarbonyloxy]adamantane,
5,7-dimethyl-1,3-bis[3-(meth)acryloyloxypropylcarbonyloxy]adamantane,
1,3-bis[2-(meth)acryloyloxy-1-methylethylcarbonyloxy]adamantane,
5,7-dimethyl-1,3-bis[2-(meth)acryloyloxy-1-methylethylcarbonyloxy]adamantane,
1,3-bis[2-(meth)acryloyloxy-2-methylethylcarbonyloxy]adamantane,
5,7-dimethyl-1,3-bis[2-(meth)acryloyloxy-2-methylethylcarbonyloxy]adamantane,
1,3-bis[3-(meth)acryloyloxy-2-methylpropylcarbonyloxy]adamantane,
5,7-dimethyl-1,3-bis[3-(meth)acryloyloxy-2-methylpropylcarbonyloxy]adamantane,
1,3-bis[3-(meth)acryloyloxy-2,2-dimethylpropylcarbonyloxy]adamantane,
5,7-dimethyl-1,3-bis[3-(meth)acryloyloxy-2,2-dimethylpropylcarbonyloxy]adamantane, and other compounds in which $A^1$ and $A^2$ are both —C(=O)—O— groups (the right-hand sides are on the adamantane ring side).

The invented adamantane derivatives represented by Formula (1) each have a (meth)acryloyl group, and can be induced into homopolymers or copolymers with other copolymerizable monomers by, for example, conventional radical polymerization. The thus-obtained polymers each have a non-aromatic and rigid adamantane ring and are therefore satisfactory in transparency, luster (gloss), hardness, water resistance, and other properties. Accordingly, these invented adamantane derivatives can be used as raw materials for dental materials such as restorative dental materials used for tooth cavity filling, dental complex filling materials, denture base materials, teeth crown materials, cementing materials, adhesives for orthodontics, adhesives for the application onto cavity, tooth fissure sealants, and dental surface lubricants; and raw materials for optical materials such as lenses.

[Production of Adamantane Derivatives Represented by Formula (1)]

The adamantane derivatives represented by Formula (1) each have four ester bonds and can be produced by forming these ester bonds using conventional esterification reactions. The sequence of the formation of the four ester bonds can be appropriately selected in view of, for example, reactivity and the costs of raw materials.

Of the adamantane derivatives represented by Formula (1), compounds (1a) in which $A^1$ and $A^2$ are both —O—C(=O)— groups, where the right-hand side is on the adamantane ring side, can be produced by Production Process 1 according to the present invention. Specifically, the adamantane derivative represented by Formula (1a) can be prepared by allowing the adamantanedicarboxylic acid represented by Formula (2) or a reactive derivative thereof to react with the (meth)acrylic hydroxyalkyl esters represented by Formulae (3a) and (3b). In this process, the two ester bonds may be formed concurrently or in stages.

For example, when the (meth)acrylic hydroxyalkyl ester represented by Formula (3a) and the (meth)acrylic hydroxyalkyl ester represented by Formula (3b) are the same compound, this compound is allowed to react with the adamantanedicarboxylic acid represented by Formula (2) or a reactive derivative thereof to thereby yield a corresponding adamantane derivative represented by Formula (1a) at one step.

Alternatively, when the (meth) acrylic hydroxyalkyl ester represented by Formula (3a) and the (meth)acrylic hydroxyalkyl ester represented by Formula (3b) are different compounds, one of the two compounds is initially allowed to react with the adamantanedicarboxylic acid represented by Formula (2) or a reactive derivative thereof to thereby convert the adamantanedicarboxylic acid represented by Formula (2) or a reactive derivative thereof into a monoester, and the monoester is then allowed to react with the other of the two compounds to thereby yield a corresponding adamantane derivative represented by Formula (1a).

Such reactive derivatives of the adamantanedicarboxylic acids represented by Formula (2) include derivatives that can form corresponding esters by reactions with alcohols, such as corresponding acid chlorides and other acid halides; acid anhydrides; and methyl esters, ethyl esters, vinyl esters, 2-propenyl esters, and other esters (e.g., alkyl esters and alkenyl esters). These reactive derivatives can be induced from the adamantanedicarboxylic acids represented by Formula (2) by conventional techniques.

The reaction (esterification) of the adamantanedicarboxylic acid represented by Formula (2) with the (meth)acrylic hydroxyalkyl ester represented by Formula (3a) and/or the (meth)acrylic hydroxyalkyl ester represented by Formula (3b) is generally performed in a solvent inert to the reaction. Such solvents include, but are not limited to, benzene, toluene, xylene, ethylbenzene, and other aromatic hydrocarbons; hexane, heptane, octane, decane, and other aliphatic hydrocarbons; cyclohexane, and other alicyclic hydrocarbons; methylene chloride, chloroform, 1,2-dichloroethane, chlorobenzene, trifluoromethylbenzene, and other halogenated hydrocarbons; ethyl acetate, butyl acetate, and other esters; diethyl ether, diisopropyl ether, dibutyl ether, anisole, and other ethers; and mixtures of these solvents. Preferred solvents are solvents that can be azeotropically boiled with by-produced water and can be separated from water (azeotropic solvents that can be dehydrated), such as toluene.

Catalysts for use in the esterification reaction include, for example, sulfuric acid, hydrochloric acid, phosphoric acid, heteropolyacids, and other inorganic acids; benzenesulfonic acid, p-toluenesulfonic acid, naphthalenesulfonic acid, methanesulfonic acid, trifluoromethanesulfonic acid, ethanesulfonic acid, sulfonic-acid-based strongly acidic ion-exchange resins, and other sulfonic acids. Lewis acids can also be used as the catalysts. Each of these catalysts can be used alone or in combination.

The esterification reaction is performed at a temperature of, for example, from about 50° C. to about 150° C. at atmospheric pressure or under a reduced pressure. The amount of the adamantanedicarboxylic acid represented by Formula (2) is, for example, from about 0.7 to about 1.5 moles relative to 1 mole of the total amount of the (meth) acrylic hydroxyalkyl esters represented by Formulae (3a) and (3b).

The reaction (esterification) of the reactive derivative of adamantanedicarboxylic acid represented by Formula (2) with the (meth)acrylic hydroxyalkyl ester represented by Formula (3a) and/or the (meth)acrylic hydroxyalkyl ester represented by Formula (3b) can be performed in the presence of a base or a transesterification catalyst, depending on the type of the reactive derivative. For example, when an acid halide or acid anhydride is used as the reactive derivative of adamantanedicarboxylic acid represented by Formula (2), the reaction is performed in the presence of a base (acid scavenger) such as triethylamine or pyridine in, for example, the aforementioned solvent, at a temperature of from about −78° C. to about 150° C.

To suppress polymerization reactions, polymerization inhibitors or polymerization retarders such as hydroquinone, methoxyphenol, and oxygen-containing gases can be added or supplied to a reaction system in each of the esterification reactions.

The adamantane derivatives represented by Formula (1a) formed by the reactions can be separated and purified by a conventional separation and purification means such as concentration, extraction, crystallization, recrystallization, distillation, column chromatography, and combinations of these means.

The adamantanedicarboxylic acid represented by Formula (2) for use as a raw material in the reaction can be obtained by introducing two carboxyl groups into the bridgehead positions of adamantane ring of a corresponding adamantane compound. Specifically, the adamantane compound is brought into contact with carbon monoxide and oxygen in the presence of an N-hydroxyimide catalyst such as N-hydroxyphthalimide, and according to necessity, a metallic co-catalyst (promoter) such as a cobalt compound (e.g., cobalt acetate, acetylacetonatocobalt, acetylacetonatovanadium, and vanadyl acetylacetonato) to thereby introduce carboxyl groups into the adamantane ring of the adamantane compound. The amount of the N-hydroxyimide catalyst in the carboxylation reaction is, for example, from about 0.0001 to about 1 mole, and preferably from about 0.001 to about 0.5 mole, relative to 1 mole of the adamantane compound. The amount of the metallic promoter is, for example, from about 0.0001 to about 0.7 mole, and preferably from about 0.001 to about 0.5 mole, relative to 1 mole of the adamantane compound. The amounts of carbon monoxide and of oxygen are equal to or higher than 2 moles, and equal to or higher than 1 mole, respectively relative to 1 mole of the adamantane compound. The ratio of carbon monoxide to oxygen is, for example, such that the former/the latter (by mole) is from about 1/99 to about 99/1, and preferably from about 50/50 to about 95/5. The carboxylation reaction is performed in a solvent at a temperature of from about 0° C. to 200° C. and preferably from about 10° C. to about 150° C. at atmospheric pressure or under a pressure (under a load). Such solvents include, for example, acetic acid and other organic acids, acetonitrile and other nitriles, and dichloroethane and other halogenated hydrocarbons.

Of the adamantane derivatives represented by Formula (1), compounds (1b) in which $A^1$ and A 2are both —C(=O)—O— groups (the right-hand sides are on the adamantane ring side) can be produced by Production Process 2 according to the present invention. Specifically, the adamantane derivative represented by Formula (1b) can be obtained by allowing the adamantanediol represented by Formula (4) to react with the (meth)acryloyloxy-group-containing carboxylic acids represented by Formulae (5a) and (5b) or reactive derivatives thereof. In this process, two ester bonds may be formed concurrently or in stages.

For example, when the compound represented by Formula (5a) or a reactive derivative thereof and the compound represented by Formula (5b) or a reactive derivative thereof are the same compound, this compound is allowed to react with the adamantanediol represented by Formula (4) to thereby yield a corresponding adamantane derivative represented by Formula (1b) at one step.

Alternatively, when the compound represented by Formula (5a) or a reactive derivative thereof and the compound represented by Formula (5b) or a reactive derivative thereof are different compounds, one of the two compounds is initially allowed to react with the adamantanediol represented by Formula (4) to thereby convert the adamantanediol represented by Formula (4) into a monoester, and the monoester is then allowed to react with the other of the two compounds to thereby yield a corresponding adamantane derivative represented by Formula (1b).

Such reactive derivatives of the compounds represented by Formulae (5a) and (5b) include derivatives that can form corresponding esters by reactions with alcohols, such as corresponding acid chlorides and other acid halides; acid anhydrides; and methyl esters, ethyl esters, vinyl esters, 2-propenyl esters, and other esters (e.g., alkyl esters and alkenyl esters).

The reaction (esterification) of the compound represented by Formula (5a) and/or the compound represented by Formula (5b) with the adamantanediol represented by Formula (4) can be performed pursuantly to the reaction (esterification) of the adamantanedicarboxylic acid represented by Formula (2) with the (meth)acrylic hydroxyalkyl esters represented by Formula (3a) and/or (3b). The reaction (esterification) of the reactive derivative of the compound represented by Formula (5a) and/or the reactive derivative of the compound represented by Formula (5b) can be performed pursuantly to the reaction (esterification) of the reactive derivative of adamantanedicarboxylic acid represented by Formula (2) with the (meth)acrylic hydroxyalkyl esters represented by Formula (3a) and/or (3b).

The adamantane derivatives represented by Formula (1b) formed by the reactions can be separated and purified by a conventional separation and purification means such as concentration, extraction, crystallization, recrystallization, distillation, column chromatography, and combinations of these means.

The adamantanediol represented by Formula (4) for use as a raw material in the reaction can be obtained by introducing two hydroxyl groups into the bridgehead positions of adamantane ring of a corresponding adamantane compound. Specifically, the adamantane compound is brought into contact with oxygen in the presence of an N-hydroxyimide catalyst such as N-hydroxyphthalimide, and according to necessity, a metallic co-catalyst (promoter) to thereby introduce hydroxyl groups into the adamantane ring of the adamantane compound. Such metallic co-catalysts include, for example, cobalt compounds (e.g., cobalt acetate and acetylacetonatocobalt) The amount of the N-hydroxyimide catalyst in the process is, for example, from about 0.0001 to about 1 mole, and preferably from about 0.001 to about 0.5 mole, relative to 1 mole of the adamantane compound. The amount of the metallic co-catalyst is, for example, from about 0.0001 to about 0.7 mole, and preferably from about 0.001 to about 0.5 mole, relative to 1 mole of the adamantane compound. Oxygen is often used in excess amounts to the adamantane. The reaction is performed in a solvent at a temperature from about 0° C. to about 200° C. and preferably from about 30° C. to about 150° C. at atmospheric pressure or under a pressure (under a load). Such solvents include, for example, acetic acid and other organic acids, acetonitrile and other nitrites, and dichloroethane and other halogenated hydrocarbons.

[Adamantane Derivatives Represented by Formula (6)]

In the adamantane derivatives represented by Formula (6), each of $A^3$ and $A^4$ is, identical to or different from each other, a group represented by the following formula:

—A—O—C(=O)—

(wherein $A^5$ is a straight- or branched-chain alkylene group having from 1 to 6 carbon atoms, where the right of the above formula is on the adamantane ring side).

Straight- or branched-chain alkylene groups each having from 1 to 6 carbon atoms in $A^5$ include, but are not limited to, methylene, ethylene, methylethylene, trimethylene, 1-methyltrimethylene, 2-methyltrimethylene, 2,2-dimethyltrimethylene, tetramethylene, pentamethylene, and hexamethylene groups. Among them, straight- or branched-chain alkylene groups each having from about 2 to about 6 carbon atoms are preferred, of which straight- or branched-chain alkylene groups each having from about 2 to about 4 carbon atoms are typically preferred.

In Formula (6), straight- or branched-chain alkylene groups each having from 1 to 12 carbon atoms in X include, but are not limited to, methylene, ethylene, methylethylene, trimethylene, 1-methyltrimethylene, 2-methyltrimethylene, 2,2-dimethyltrimethylene, tetramethylene, pentamethylene, hexamethylene, heptamethylene, octamethylene, nonamethylene, 2,2,4-trimethylhexamethylene, decamethylene, and dodecamethylene groups. Among them, straight- or branched-chain alkylene groups each having from about 2 to about 10 carbon atoms are preferred, of which straight- or branched-chain alkylene groups each having from about 4 to about 10 carbon atoms are typically preferred.

Of the compounds represented by Formula (6), illustrative compounds, in which m and n are both 0, are the following compounds represented by Formulae (6-1) to (6-12):

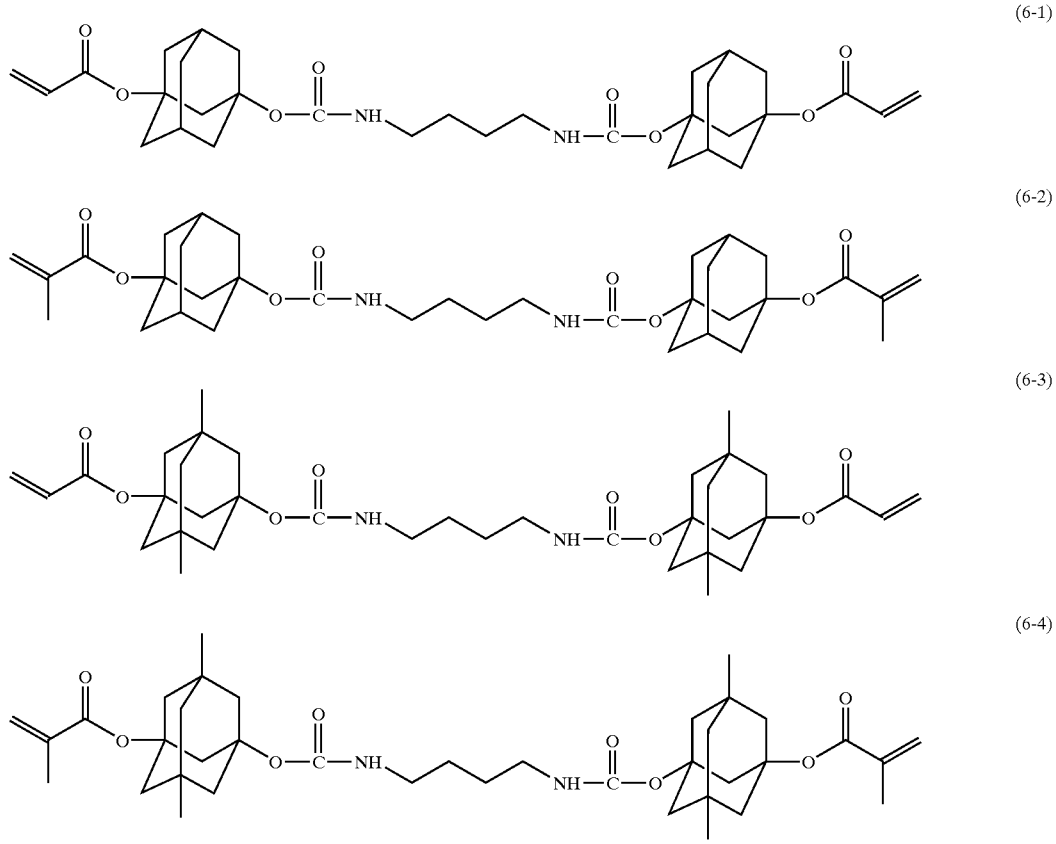

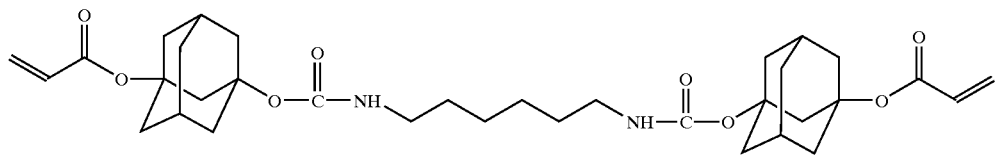
(6-5)
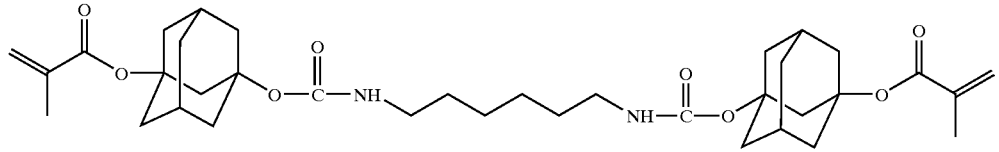
(6-6)
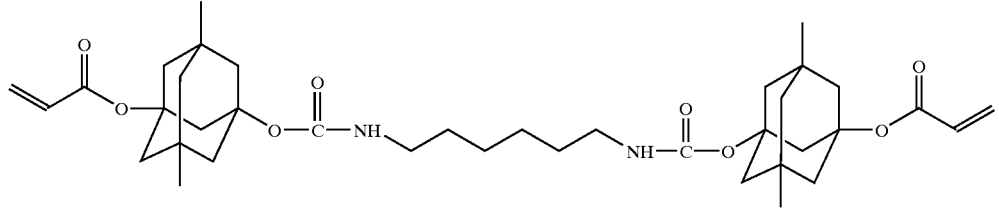
(6-7)
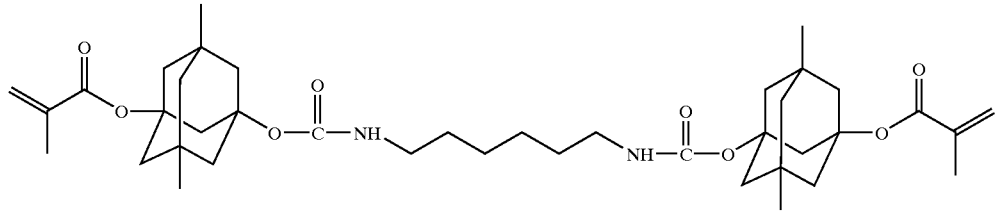
(6-8)
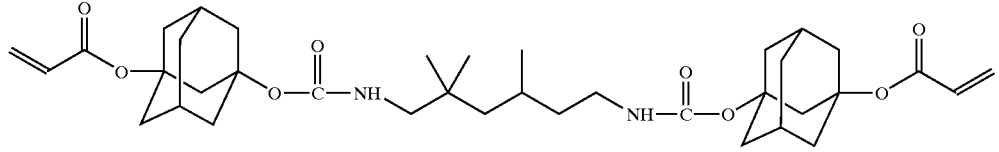
(6-9)
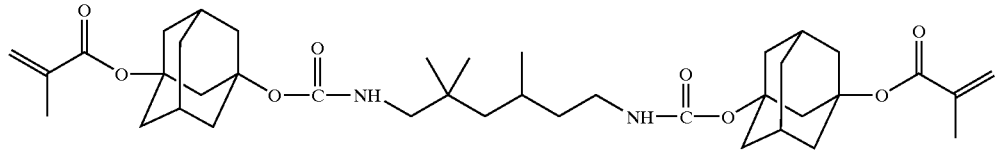
(6-10)
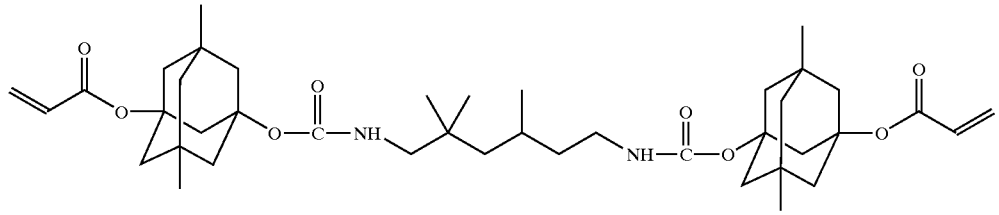
(6-11)
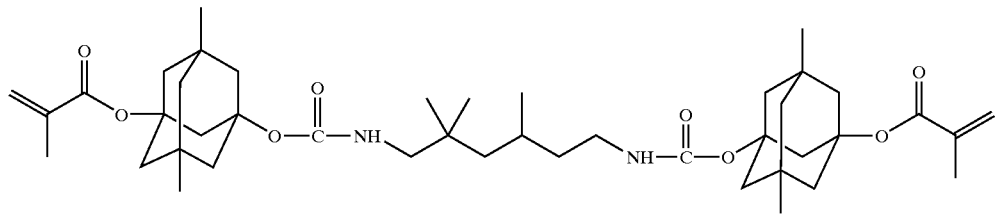
(6-12)

Of the compounds represented by Formula (6), illustrative compounds, in which m and n are both 1, are the following compounds represented by Formulae (6-13) to (6-20):
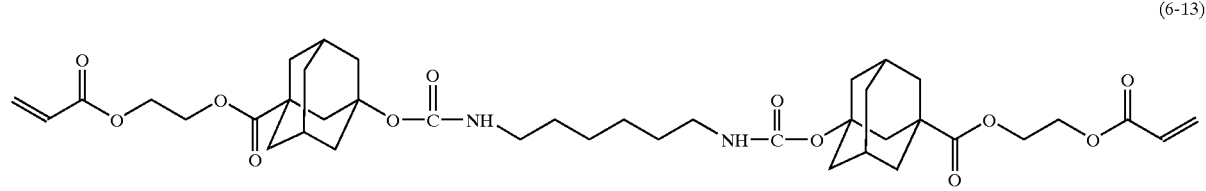
(6-13)
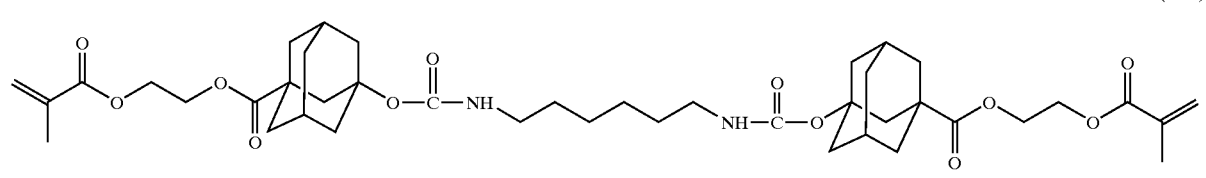
(6-14)
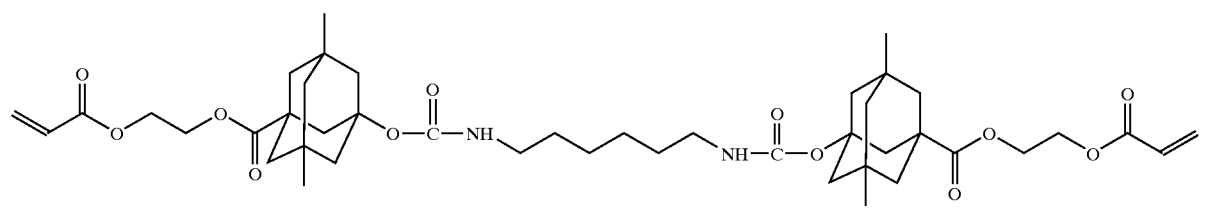
(6-15)
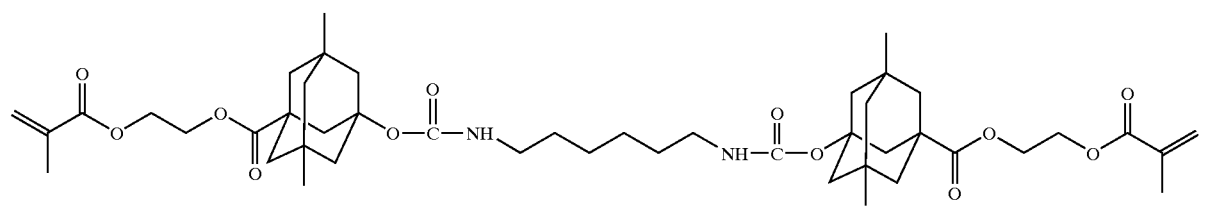
(6-16)
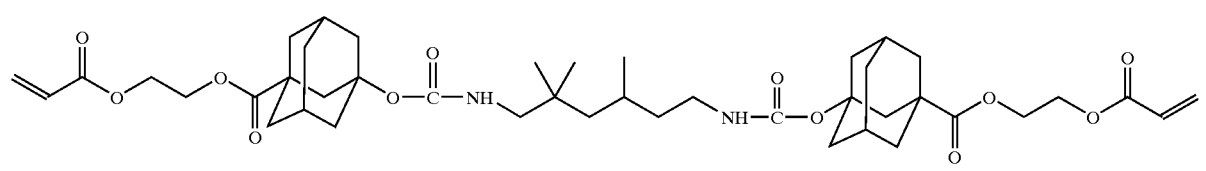
(6-17)
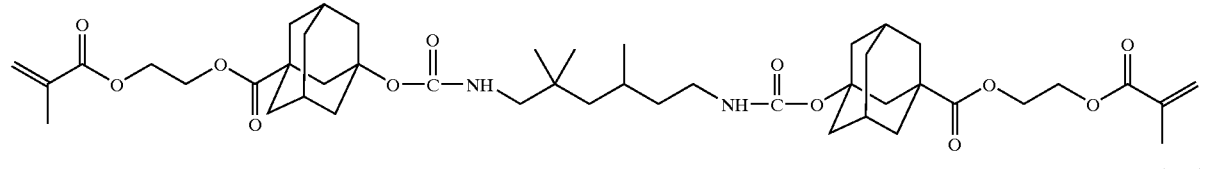
(6-18)
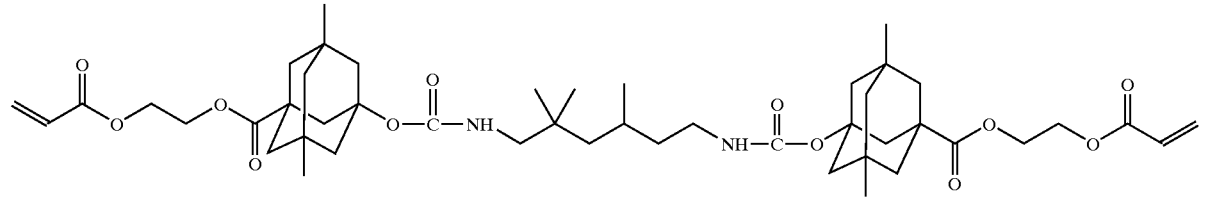
(6-19)

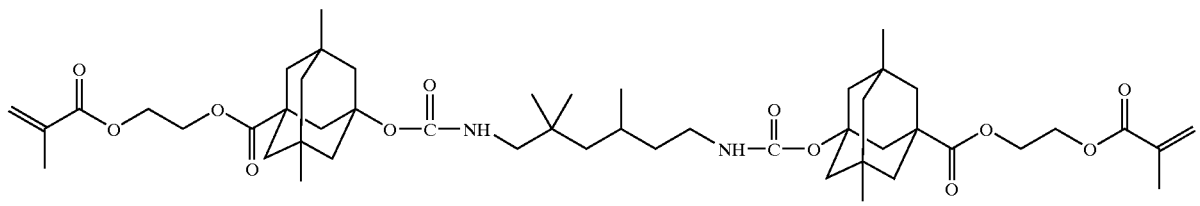

(6-20)

The invented adamantane derivatives represented by Formula (6) each have a (meth)acryloyl group, and can be induced into homopolymers or copolymers with other copolymerizable monomers by, for example, conventional radical polymerization. The thus-obtained polymers each have a non-aromatic and rigid adamantane ring and are therefore satisfactory in transparency, luster, hardness, water resistance, and other properties. Accordingly, these invented adamantane derivatives can be used as raw materials for dental materials such as restorative dental materials used for tooth cavity filling, dental complex filling materials, denture base materials, teeth crown materials, cementing materials, adhesives for orthodontics, adhesives for the application onto cavity, tooth fissure sealants, and dental surface lubricants; and raw materials for optical materials such as lenses.

[Production of Adamantane Derivatives Represented by Formula (6)]

The adamantane derivatives represented by Formula (6) each have two urethane bonds (carbamic ester bonds) and can be produced by forming these urethane bonds using a conventional reaction for the formation of urethane bond. The two urethane bonds may be formed concurrently or in stages.

For example, when the adamantanol derivative represented by Formula (7a) and the adamantanol derivative represented by Formula (7b) are the same compound in the invented production process, the adamantanol derivative in question is allowed to react with the diisocyanate compound represented by Formula (8) to thereby yield a corresponding adamantane derivative represented by Formula (6) at one step.

Alternatively, when the adamantanol derivative represented by Formula (7a) and the adamantanol derivative represented by Formula (7b) are different compounds, one of the two compounds is initially allowed to react with the diisocyanate compound represented by Formula (8) to thereby convert one of the two isocyanate groups of the diisocyanate compound into a urethane group, and the resulting reaction product (monoisocyanate compound) is then allowed to react with the other of the two compounds to thereby yield a corresponding adamantane derivative represented by Formula (6).

The reaction of the adamantanol derivatives represented by Formulae (7a) and (7b) with the diisocyanate compound represented by Formula (8) is performed in a solvent inert to the reaction or without solvent. Such solvents include, but are not limited to, hexane, octane, and other aliphatic hydrocarbons; toluene, xylene, and other aromatic hydrocarbons; cyclohexane and other alicyclic hydrocarbons; methylene chloride, 1,2-dichloroethane, and other halogenated hydrocarbons; ethyl acetate and other esters; dioxane and other ethers; and N,N-dimethylformamide and other aprotic polar solvents. Each of these solvents can be used alone or in combination.

To enhance the reaction, cuprous chloride and other metal salts may be added, or acids or bases as catalysts may be added to the reaction system. Such bases include, for example, pyridine and other basic nitrogen-containing heterocyclic compounds, and triethylamine and other tertiary amines. The reaction system may further comprise hydroquinone and other conventional or known polymerization inhibitors and/or polymerization retarders.

A reaction temperature can be appropriately selected depending on the reactivity of reactants, and is generally from about 0° C. to about 150° C. and preferably from about 10° C. to about 120° C.

The reaction products can be separated and purified by a conventional separation and purification means such as concentration, extraction, crystallization, recrystallization, distillation, column chromatography, and combinations of these means.

Of the compounds represented by Formulae (7a) and (7b), a compound, in which m and n are both 0, can be obtained by allowing a corresponding adamantanediol compound to react with (meth)acrylic acid or a reactive derivative thereof.

The adamantanediol compound for use as a raw material in the above reaction can be obtained by oxidizing a corresponding adamantane having no hydroxyl group or having one hydroxyl group with oxygen in the presence of an N-hydroxyimide catalyst such as N-hydroxyphthalimide and, according to necessity, a metallic compound co-catalyst to thereby introduce hydroxyl group(s) into the bridgehead position(s) of the adamantane ring. Such metallic compound co-catalysts include, for example, vanadium compounds (e.g., acetylacetonatovanadium and vanadyl acetylacetonato) and cobalt compounds (e.g., cobalt acetate and acetylacetonatocobalt). In this process, the amount of the N-hydroxyimide catalyst is, for example, from about 0.001 to about 0.5 mole, and preferably from about 0.01 to about 0.3 mole, relative to 1 mole of the adamantane. The amount of the metallic compound co-catalyst is, for example, from about 0.0001 to about 0.5 mole, and preferably from about 0.0005 to about 0.1 mole, relative to 1 mole of the adamantane. The oxidation reaction is performed in an organic solvent at a temperature of from about 40° C. to about 150° C. and preferably from about 60° C. to about 120° C. at atmospheric pressure or under a pressure (under a load) [e.g., from about 5 to about 40 atm (from about 0.505 to about 4.04 MPa)]. Such organic solvents include, for example, acetic acid and other organic acids, acetonitrile, benzonitrile, and other nitrites, trifluoromethylbenzene and other halogenated hydrocarbons.

The reactive derivatives of (meth)acrylic acid include derivatives that can form corresponding esters by reactions with alcohols, such as (meth)acryloyl chloride and other (meth)acryloyl halides; (meth)acrylic anhydride and other acid anhydrides; methyl (meth)acrylate, ethyl (meth)acrylate, vinyl (meth)acrylate, 2-propenyl (meth)acrylate, and other (meth) acrylic esters (e.g., alkyl esters and alkenyl esters).

The reaction (esterification) of the adamantanediol compound with (meth) acrylic acid is generally performed in a solvent inert to the reaction. Such solvents include, but are not limited to, benzene, toluene, xylene, ethylbenzene, and other aromatic hydrocarbons; hexane, heptane, octane, decane, and other aliphatic hydrocarbons; cyclohexane and other alicyclic hydrocarbons; methylene chloride, chloroform, 1,2-dichloroethane, chlorobenzene, trifluoromethylbenzene, and other halogenated hydrocarbons; ethyl acetate, butyl acetate, and other esters; diethyl ether, diisopropyl ether, dibutyl ether, anisole, and other ethers; and mixtures of these solvents. Preferred solvents are solvents that can be azeotropically boiled with by-produced water and can be separated from water (azeotropic solvents that can be dehydrated), such as toluene.

Catalysts for use in the esterification reaction include, but are not limited to, sulfuric acid, hydrochloric acid, phosphoric acid, heteropolyacids, and other inorganic acids; benzenesulfonic acid, p-toluenesulfonic acid, naphthalenesulfonic acid, methanesulfonic acid, trifluoromethanesulfonic acid, ethanesulfonic acid, sulfonic-acid-based strongly acidic ion-exchange resins, and other sulfonic acids. Lewis acids can also be used as the catalysts. Each of these catalysts can be used alone or in combination.

The esterification reaction with the adamantanediol compound with (meth) acrylic acid is performed at a temperature of from about 50° C. to about 150° C. at atmospheric pressure or under a reduced pressure. The amount of (meth) acrylic acid is generally equal to or more than 1 mole, and preferably equal to or more than 1.5 moles (e.g., from about 1.5 to about 10 moles, and typically from about 2.5 to about 6 moles), relative to 1 mole of the adamantanediol compound.

The reaction of the adamantanediol compound with the reactive derivative of (meth) acrylic acid can be performed in the presence of a base or a transesterification catalyst, depending on the type of the reactive derivative. For example, when a (meth)acryloyl halide or (meth)acrylic anhydride is used as the reactive derivative of (meth)acrylic acid, the reaction is performed in the presence of a base (acid scavenger) such as triethylamine or pyridine in, for example, the aforementioned solvent at a temperature of from about −78° C. to about 150° C. When a (meth)acrylic ester is used as the reactive derivative of (meth)acrylic acid, the reaction is performed in the presence of a conventional transesterification catalyst in, for example, the aforementioned solvent at a temperature of from about 0° C. to about 150° C. In particular, when an alkenyl (meth)acrylate is used as the reactive derivative, the reaction is performed in the presence of a catalyst of compound of Group 3 element of the Periodic Table of Elements (e.g., samarium acetate, samarium trifluoromethanesulfonate, samarium complexes, and other samarium compounds) under the above conditions.

Of the compounds represented by Formulae (7a) and (7b), a compound, in which m and n are 1, can be obtained by subjecting a corresponding monohydric carboxyadamantanol compound (carboxyadamantanemonool compound), a compound in which the hydroxyl group of the aforementioned compound is protected with a conventional protective group (e.g., methoxyethoxymethyl group), or a reactive derivative of these compounds to an esterification reaction with a corresponding (meth)acrylic hydroxy-$C_1$–$C_6$ alkyl ester and, according to necessity, deprotecting the protective group of the hydroxyl group.

The monohydric carboxyadamantanol compound for use as a raw material in this reaction can be obtained by introducing a carboxyl group into the bridgehead position of adamantane ring of a corresponding monohydric adamantanol compound. Specifically, the monohydric carboxyadamantanol compound is brought into contact with carbon monoxide and oxygen in the presence of an N-hydroxyimide catalyst such as N-hydroxyphthalimide, and according to necessity, a metallic co-catalyst (promoter) such as a cobalt compound (e.g., cobalt acetate, acetylacetonatocobalt, acetylacetonatovanadium, and vanadyl acetylacetonato) to thereby introduce a carboxyl group into the adamantane ring of the monohydric adamantanol compound. The amount of the N-hydroxyimide catalyst in the carboxylation reaction is, for example, from about 0.0001 to about 1 mole, and preferably from about 0.001 to about 0.5 mole, relative to 1 mole of the adamantane compound. The amount of the metallic co-catalyst is, for example, from about 0.0001 to about 0.7 mole, and preferably from about 0.001 to about 0.5 mole, relative to 1 mole of the adamantane compound. The amounts of carbon monoxide and of oxygen are equal to or higher than 1 mole, and equal to or higher than 0.5 mole, respectively relative to 1 mole of the adamantane compound. The ratio of carbon monoxide to oxygen is, for example, such that the former/the latter (by mole) is from about 1/99 to about 99/1, and preferably from about 50/50 to about 95/5. The carboxylation reaction is performed in a solvent at a temperature of from about 0° C. to 200° C. and preferably from about 10° C. to about 150° C. at atmospheric pressure or under a pressure (under a load). Such solvents include, for example, acetic acid and other organic acids, acetonitrile and other nitriles, and dichloroethane and other halogenated hydrocarbons.

The esterification reaction of the thus-obtained monohydric carboxyadamantanol compound, a compound in which the hydroxyl group of this compound is protected, or a reactive derivative of these compounds with the (meth) acrylic hydroxy-$C_1$–$C_6$ alkyl ester can be performed pursuantly to the reaction of the adamantanediol compound with (meth)acrylic acid or a reactive derivative thereof. Introduction of the protective group into hydroxyl group and deprotection of the introduced protective group can be performed using a conventional process in the field of organic synthesis.

[Adamantane Derivatives Represented by Formula (9)]

In the adamantane derivatives of the present invention represented by Formula (9), $R^{11}$ is a hydrogen atom, a straight- or branched-chain alkyl group having from 1 to 4 carbon atoms, or the group represented by Formula (10). Such straight- or branched-chain alkyl groups each having from 1 to 4 carbon atoms include methyl, ethyl, propyl, isopropyl, butyl, isobutyl, s-butyl, and t-butyl groups. Among them, straight- or branched-chain alkyl groups each having from 1 to 3 carbon atoms such as methyl, ethyl, and propyl groups are typically preferred. The numeral s in Formula (10) denotes an integer from 1 to 6, and preferably an integer from 1 to 4, and more preferably an integer from 1 to 3, of which 1 is typically preferred.

Typically preferred $R^{11}$ includes, for example, ethyl group, (meth)acryloyloxymethyl group,
1-adamantylcarbonyloxymethyl group, and
1,3-dimethyladamant-1-ylcarbonyloxymethyl group.

Each of p, q and r independently denotes an integer from 1 to 6, preferably an integer from 1 to 4, more preferably an integer from 1 to 3, and particularly 1.

Illustrative invented adamantane derivatives represented by Formula (9) include, for example,
trimethylolpropane diacrylate mono (1-adamantanecarboxylate),
trimethylolpropane dimethacrylate mono(1-adamantanecarboxylate), trimethylolpropane diacrylate mono(3,5-dimethyl-1-adamantanecarboxylate), trimethylolpropane dimethacrylate mono(3,5-dimethyl-1-adamantanecarboxylate), and other compounds in which $R^{11}$ is ethyl group; pentaerythritol triacrylate mono(1-adamantanecarboxylate), pentaerythritol trimethacrylate mono(1-adamantanecarboxylate), pentaerythritol triacrylate mono(3,5-dimethyl-1-adamantanecarboxylate), pentaerythritol trimethacrylate mono(3,5-dimethyl-1-adamantanecarboxylate), and other compounds in which $R^{11}$ is (meth)acryloyloxymethyl group;

pentaerythritol diacrylate di(1-adamantanecarboxylate), pentaerythritol dimethacrylate di(1-adamantanecarboxylate), pentaerythritol diacrylate di(3,5-dimethyl-1-adamantanecarboxylate), pentaerythritol dimethacrylate di(3,5-dimethyl-1-adamantanecarboxylate), and other compounds in which $R^{11}$ is 1-adamantylcarbonyloxymethyl group or 1,3-dimethyladamant-1-ylcarbonyloxymethyl group.

The invented adamantane derivatives represented by Formula (9) each have a (meth)acryloyl group, and can be induced into homopolymers or copolymers with other copolymerizable monomers by, for example, conventional radical polymerization. The thus-obtained polymers each have a non-aromatic and rigid adamantane ring and are therefore satisfactory in transparency, luster, hardness, water resistance, and other properties. Accordingly, these invented adamantane derivatives can be used as raw materials for dental materials such as restorative dental materials used for tooth cavity filling, dental complex filling materials, denture base materials, teeth crown materials, cementing materials, adhesives for orthodontics, adhesives for the application onto cavity, tooth fissure sealants, and dental surface lubricants; and raw materials for optical materials such as lenses.

[Production of Adamantane Derivatives Represented by Formula (9)]

In the process for producing an adamantane derivatives represented by Formula (9) according to the present invention, reactive derivatives of adamantanecarboxylic acids represented by Formula (11) include derivatives that can form corresponding esters by reactions with alcohols, such as 1-adamantanecarboxylic chloride, 3,5-dimethyl-1-adamantanecarboxylic chloride, and other adamantanecarboxylic halides; 1-adamantanecarboxylic anhydride, and other acid anhydrides; methyl 1-adamantanecarboxylate, methyl 3,5-dimethyl-1-adamantanecarboxylate, ethyl 1-adamantanecarboxylate, ethyl 3,5-dimethyl-1-adamantanecarboxylate, vinyl 1-adamantanecarboxylate, vinyl 3,5-dimethyl-1-adamantanecarboxylate, 2-propenyl 1-adamantanecarboxylate, 2-propenyl 3,5-dimethyl-1-adamantanecarboxylate, and other adamantanecarboxylic esters (e.g., alkyl esters and alkenyl esters). The reactive derivatives of adamantanecarboxylic acids represented by Formula (11) can be induced from the adamantanecarboxylic acids represented by Formula (11) by conventional techniques.

The reaction (esterification) of the adamantanecarboxylic acid represented by Formula (11) with the compound represented by Formula (12) is generally performed in a solvent inert to the reaction. Such solvents include, but are not limited to, benzene, toluene, xylene, ethylbenzene, and other aromatic hydrocarbons; hexane, heptane, octane, decane, and other aliphatic hydrocarbons; cyclohexane and other alicyclic hydrocarbons; methylene chloride, chloroform, 1,2-dichloroethane, chlorobenzene, trifluoromethylbenzene, and other halogenated hydrocarbons; ethyl acetate, butyl acetate, and other esters; diethyl ether, diisopropyl ether, dibutyl ether, anisole, and other ethers; and mixtures of these solvents. Preferred solvents are solvents that can be azeotropically boiled with by-produced water and can be separated from water (azeotropic solvents that can be dehydrated), such as toluene.

Catalysts for use in the esterification reaction include, but are not limited to, sulfuric acid, hydrochloric acid, phosphoric acid, heteropolyacids, and other inorganic acids; benzenesulfonic acid, p-toluenesulfonic acid, naphthalenesulfonic acid, methanesulfonic acid, trifluoromethanesulfonic acid, ethanesulfonic acid, sulfonic-acid-based strongly acidic ion-exchange resins, and other sulfonic acids. Lewis acids can also be used as the catalysts. Each of these catalysts can be used alone or in combination.

The esterification reaction of the adamantanecarboxylic acid represented by Formula (11) with the compound represented by Formula (12) is performed at a temperature of, for example, from about 50° C. to about 150° C. at atmospheric pressure or under a reduced pressure. The amount of the adamantanecarboxylic acid represented by Formula (11) is, for example, from about 0.7 to about 1.5 moles relative to 1 mole of the compound represented by Formula (12).

The reaction of the reactive derivative of adamantanecarboxylic acid represented by Formula (11) with the compound represented by Formula (12) can be performed in the presence of a base or a transesterification catalyst, depending on the type of the reactive derivative. For example, when an adamantanecarboxylic halide or acid anhydride is used as the reactive derivative of adamantanecarboxylic acid represented by Formula (11), the reaction is performed in the presence of a base (acid scavenger) such as triethylamine or pyridine in , for example, the aforementioned solvent, at a temperature of from about −78° C. to about 150° C.

To suppress polymerization reactions, polymerization inhibitors or polymerization retarders such as hydroquinone, methoxyphenol, and oxygen-containing gases can be added or supplied to a reaction system in each of the esterification reactions.

The compound represented by Formula (12) for use as a raw material in the invented production process can be obtained by subjecting a corresponding triol or tetraol compound to an esterification reaction with (meth) acrylic acid or a reactive derivative thereof (or (meth)acrylic acid or a reactive derivative thereof and 1-adamantanecarboxylic acid, 3,5-dimethyl-1-adamantanecarboxylic acid or a reactive derivative thereof). This esterification reaction can be performed pursuantly to the esterification reaction of the reactive derivative of adamantanecarboxylic acid represented by Formula (11) with the compound represented by Formula (12). In this reaction, a compound represented by Formula (12) having one hydroxyl group can be obtained in a high yield by controlling the molar ratio of charged raw materials.

The reaction products can be separated and purified by a conventional separation and purification means such as concentration, extraction, crystallization, recrystallization, distillation, column chromatography, and combinations of these means.

Industrial Applicability

The present invention can provide novel adamantane derivatives which are useful for obtaining polymers having, for example, satisfactory transparency, luster, hardness, and water resistance. These compounds are useful, for example, as dental materials or raw materials therefor, and as raw materials for optical materials such as lenses.

EXAMPLES

The present invention will be illustrated in further detail with reference to several examples below, which are not intended to limit the scope of the invention.

Example 1
[Production of bis(2-Methacryloyloxyethyl)1,3-adamantanedicarboxylate]

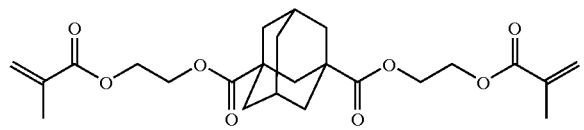

In a 1-L round bottom flask equipped with a stirrer, thermometer, dropping funnel, cooling tube, and calcium chloride tube, 32.9 g (252.73 mmol) of 2-hydroxyethyl methacrylate, 22.7 g (287.19 mmol) of pyridine, 30 mg (0.24 mmol) of methoxyphenol, and 200 ml of toluene were placed, and 150 ml of a toluene solution of 30 g (114.88 mmol) of 1,3-adamantanedicarboxylic chloride was added dropwise to the mixture at room temperature over 30 minutes with stirring. Next, the resulting mixture was heated to 100° C. and was stirred for 2 hours, was then cooled to room temperature, was washed successively with 200 ml of an aqueous 0.5 N hydrochloric acid solution, 200 ml of distilled water, and 200 ml of an aqueous saturated sodium chloride solution, and was dried over an appropriate amount of sodium sulfate. After removing the desiccating agent by filtration and the solvent by distillation under a reduced pressure, the resulting concentrate was purified by column chromatography on a silica gel (ethyl acetate/hexane=5/1) to thereby yield 43.8 g (97.65 mmol) of the title compound as a colorless, transparent liquid in a yield of 85.0% (on the basis of 1,3-adamantanedicarboxylic chloride).
[Spectral Data of the Title Compound]
$^1$H-NMR (CDCl$_3$) δ: 1.68 (br, s, 2H), 1.80–1.92 (m, 8H), 1.94 (br, s, 6H), 2.03 (br, s, 2H), 2.15 (m, 2H), 4.30–4.37 (m, 8H), 5.59 (br, s, 2H), 6.12 (br, s, 2H).

Example 2
[Production of bis(4-Methacryloyloxybutyl)1,3-adamantanedicarboxylate]

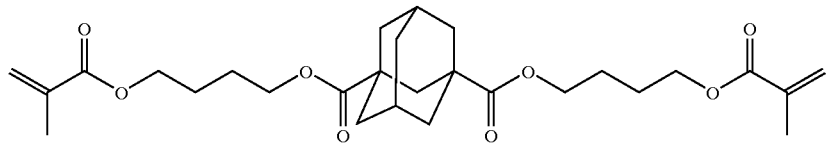

In a 3-L round bottom flask equipped with a stirrer, thermometer, cooling tube, and Dean-Stark apparatus, 100 g (1.162 mol) of methacrylic acid, 157.03 g (1.742 mol) of 1,4-butanediol, 100 mg (0.91 mmol) of hydroquinone, and 1.0 L of toluene were placed and were stirred at room temperature. While blowing air at a flow rate of 200 ml/minute into the mixture, 1.59 g (16.2 mmol) of sulfuric acid was added to the mixture, and the resulting mixture was stirred for 3 hours under reflux by heating, and was then cooled to room temperature. The solvent was distilled away from the reaction mixture under a reduced pressure, and 1.5 L of hexane was added to the mixture, and the mixture was extracted with distilled water (1.0 L×4), and the resulting aqueous layer was concentrated to 2.0 L under a reduced pressure. The concentrate was further extracted with ethyl acetate (1.0 L×3), and the resulting organic layer was successively washed with an aqueous saturated sodium carbonate solution (500 ml×3), and an aqueous saturated sodium chloride solution (500 ml×1), and the solvent was distilled away under a reduced pressure to thereby yield 110.54 g (0.699 mol) of 4-hydroxybutyl methacrylate as a yellow, transparent liquid in a yield of 58.8%.
[Spectral Data of 4-Hydroxybutyl Methacrylate]
$^1$H-NMR (CDCl$_3$) δ: 1.60–1.82 (m, 4H), 1.94 (br, s, 3H), 2.34 (br, s, 1H), 3.68 (dd, J=6.5, 10.8 Hz, 2H), 4.18 (t, J=7.0 Hz, 2H), 5.56 (br, s, 1H), 6.10 (br, s, 1H).

In a 1-L round bottom flask equipped with a stirrer, thermometer, dropping funnel, cooling tube, and calcium chloride tube, 40.0 g (252.73 mmol) of the above-prepared 2-hydroxybutyl methacrylate, 22.7 g (287.19 mmol) of pyridine, 30 mg (0.24 mmol) of methoxyphenol, and 200 ml of toluene were placed, and 150 ml of a toluene solution of 30 g (114.88 mmol) of 1,3-adamantanedicarboxylic chloride was added dropwise to the mixture at room temperature over 30 minutes with stirring. Next, the resulting mixture was heated to 100° C. and was stirred for 2 hours, was then cooled to room temperature, was washed successively with 200 ml of an aqueous 0.5 N hydrochloric acid solution, 200 ml of distilled water, and 200 ml of an aqueous saturated sodium chloride solution, and was dried over an appropriate amount of sodium sulfate. After removing the desiccating agent by filtration and the solvent by distillation under a reduced pressure, the resulting concentrate was purified by column chromatography on a silica gel (ethyl acetate/hexane=5/1) to thereby yield 48.0 g (95.12 mmol) of the title compound as a colorless, transparent liquid in a yield of 82.8% (on the basis of 1,3-adamantanedicarboxylic chloride).
[Spectral Data of the Title Compound]
$^1$H-NMR (CDCl$_3$) δ: 1.66–1.91 (m, 18H), 1.95 (br, s, 6H), 2.02 (br, s, 2H), 2.16 (m, 2H), 4.12 (t, J=6.0 Hz, 4H), 4.18 (t, J=6.5 Hz, 4H), 5.57 (br, s, 2H), 6.11 (br, s, 2H).

Reference Example 1

In a 1-L round bottom flask equipped with a stirrer, cooling tube and thermometer, 59.2 g of 1,3-adamantanediol, 121.1 g of methacrylic acid, 6.75 g of p-toluenesulfonic acid, 0.35 g of sulfuric acid, 1.18 g of methoquinone, and 510 g of toluene were placed, and air was supplied into the resulting mixture at a flow rate of 300 ml/minute. The mixture was raised in temperature to 110° C., and the reaction was performed for about 5 hours, whereas water by-produced by the reaction was distilled away by azeotropic evaporation with toluene, and toluene alone was recycled to the reactor. The resulting reaction mixture was successively washed with water, an aqueous 10% by weight sodium carbonate solution, and an aqueous 10% by weight sodium chloride solution, and was concentrated, and the resulting concentrate was subjected to column chromatography on a silica gel to thereby yield 67.5 g of 3-methacryloyloxy-1-adamantanol in a yield of 81.0%.

Reference Example 2

The procedure of Reference Example 1 was repeated, except that 100.0 g of 1,3-dimethyl-5,7-adamantanediol was used instead of 1,3-adamantanediol, to thereby yield 121.5 g of 1,3-dimethyl-7-methacryloyloxy-5-adamantanol in a yield of 90.2%.

Example 3
[Production of bis(3-Methacryloyloxyadamant-1-yl) hexamethylene Diurethane]

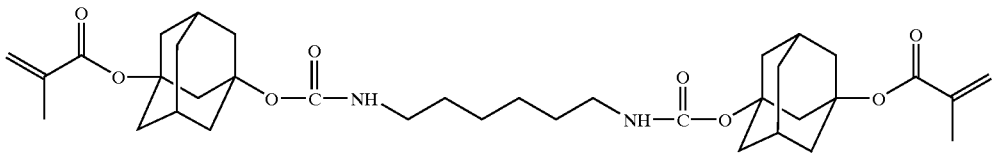

In a 300-ml round bottom flask equipped with a stirrer, cooling tube and thermometer, 19.94 g (84.381 mmol) of 3-methacryloyloxy-1-adamantanol, 6.45 g (38.355 mmol) of hexamethylene diisocyanate, 854 mg (8.438 mmol) of triethylamine, 20 mg of hydroquinone, and 100 ml of toluene were placed, and were stirred for 40 hours under reflux by heating. The reaction mixture was cooled to room temperature, and the solvent was then distilled away from the reaction mixture under a reduced pressure, and the resulting concentrate was purified by column chromatography on a silica gel (ethyl acetate/hexane=3/1) to thereby yield 5.39 g (8.411 mmol) of the title compound as a white solid in a yield of 21.9% (on the basis of hexamethylene diisocyanate).
[Spectral Data of the Title Compound]
$^1$H-NMR (CDCl$_3$) δ: 1.32 (m, 4H), 1.48 (m, 4H), 1.58 (m, 4H), 1.88 (br, s, 6H), 2.00–2.22 (m, 16H), 2.35 (m, 4H), 2.50 (m, 4H), 3.10 (m, 4H), 4.68 (br, s, 2H), 5.50 (br, s, 2H), 6.01 (br, s, 2H).

Example 4
[Production of bis(1,3-Dimethyl-5-methacryloyloxyadamant-7-yl)2,2,4-trimethylhexamethylene Diurethane]

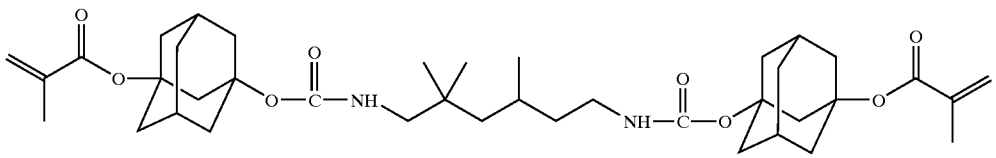

In a 200-ml round bottom flask equipped with a stirrer, cooling tube and thermometer, 10.0 g (37.826 mmol) of 1,3-dimethyl-7-methacryloyloxy-5-adamantanol, 10 mg (0.09 mmol) of hydroquinone, 3.58 g (36.107 mmol) of copper(I) chloride, and 100 ml of N,N-dimethylformamide were placed, and 3.61 g (17.194 mmol) of 2,2,4-trimethylhexamethylene diisocyanate was added dropwise to the mixture at room temperature with stirring. The resulting mixture was stirred at room temperature for further 3 hours and was then diluted with 400 ml of ethyl acetate, was successively washed with distilled water (200 ml×2) and an aqueous saturated sodium chloride solution (200 ml×1), and was dried over an appropriate amount of sodium sulfate. After removing the desiccating agent by filtration and the solvent by distillation under a reduced pressure, the resulting concentrate was purified by column chromatography on a silica gel (ethyl acetate/hexane=5/1) to thereby yield 5.66 g (7.653 mmol) of the title compound as a white solid in a yield of 20.2% (on the basis of 2,2,4-trimethylhexamethylene diisocyanate)
[Spectral Data of the Title Compound]
$^1$H-NMR (CDCl$_3$) δ: 0.85–1.90 (m, 52H), 2.38 (m, 4H), 2.76–3.18 (m, 4H), 4.48–4.80 (m, 2H), 5.47 (br, s, 2H), 5.99 (br, s, 2H).

Reference Example 3

In a 500-ml round bottom flask equipped with a stirrer, thermometer, cooling tube and Dean-Stark apparatus, 50 g (367.2 mmol) of pentaerythritol, 94.85 g (1101.7 mmol) of methacrylic acid, 250 mg (2.27 mmol) of hydroquinone, and 100 ml of toluene were placed and were stirred at room temperature. While blowing air at a flow rate of 200 ml/minute thereinto, 1.80 g (18.36 mmol) of sulfuric acid was added to the mixture, and the resulting mixture was stirred for 4 hours under reflux by heating, and was then cooled to room temperature. The reaction mixture was successively washed with an aqueous saturated sodium carbonate solution (100 ml×3) and an aqueous saturated sodium chloride solution (100 ml×1) and was then dried over an appropriate amount of sodium sulfate. After removing the desiccating agent by filtration and the solvent by distillation under a reduced pressure, the resulting concentrate was purified by column chromatography on a silica gel (ethyl acetate/hexane=5/1) to thereby yield 48.44 g (142.3 mmol) of pentaerythritol trimethacrylate as a colorless, transparent liquid in a yield of 38.8%.
[Spectral Data of Pentaerythritol Trimethacrylate]
$^1$H-NMR (CDCl$_3$) δ: 1.95 (br, s, 9H), 2.75 (br, s, 1H), 3.61 (s, 2H), 4.27 (s, 6H), 5.61 (br, s, 3H), 6.12 (br, s, 3H).

Reference Example 4

In a 500-ml round bottom flask equipped with a stirrer, thermometer, cooling tube and Dean-Stark apparatus, 50 g (372.6 mmol) of trimethylolpropane, 64.16 g (745.3 mmol) of methacrylic acid, 250 mg (2.27 mmol) of hydroquinone, and 100 ml of toluene were placed and were stirred at room temperature. While blowing air at a flow rate of 200 ml/minute thereinto, 1.80 g (18.36 mmol) of sulfuric acid was added to the mixture, and the resulting mixture was stirred for 4 hours under reflux by heating, and was then cooled to room temperature. The reaction mixture was successively washed with an aqueous saturated sodium carbonate solution (100 ml×3) and an aqueous saturated sodium chloride solution (100 ml×1) and was then dried over an appropriate amount of sodium sulfate. After removing the desiccating agent by filtration and the solvent by distillation under a reduced pressure, the resulting concentrate was purified by column chromatography on a silica gel (ethyl acetate/hexane=5/1) to thereby yield 56.77 g (210.0 mmol) of trimethylolpropane dimethacrylate as a colorless, transparent liquid in a yield of 56.4%.

[Spectral Data of Trimethylolpropane Dimethacrylate]

$^1$H-NMR (CDCl$_3$) δ: 0.93 (t, J=7.7 Hz, 3H), 1.49 (q, J=7.7 Hz, 2H), 1.95 (br, s, 6H), 2.64 (br, s, 1H), 3.49 (s, 2H), 4.14 (s, 4H), 5.60 (br, s, 2H), 6.11 (br, s, 2H).

Example 5

[Production of Pentaerythritol Trimethacrylate mono(1-Adamantanecarboxylate)]

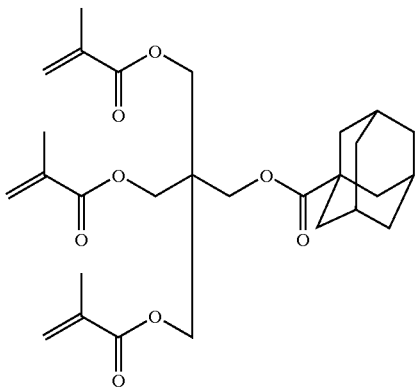

In a 500-ml round bottom flask equipped with a stirrer, thermometer, dropping funnel, cooling tube and calcium chloride tube, 45.0 g (132.2 mmol) of pentaerythritol trimethacrylate, 15.69 g (198.3 mmol) of pyridine, 50 mg (0.40 mmol) of methoxyphenol, and 180 ml of toluene were placed, and 115 ml of a toluene solution of 28.89 g (145.4 mmol) of 1-adamantanecarboxylic chloride was added dropwise to the resulting mixture at room temperature over 30 minutes with stirring. Next, the resulting mixture was heated to 100° C. and was stirred for 3 hours, was then cooled to room temperature, was successively washed with an aqueous saturated sodium carbonate solution (200 ml×2) and an aqueous saturated sodium chloride solution (200 ml×1), and was then dried over an appropriate amount of sodium sulfate. After removing the desiccating agent by filtration and the solvent by distillation under a reduced pressure, the resulting concentrate was purified by column chromatography on a silica gel (ethyl acetate/hexane=10/1) to thereby yield 59.17 g (117.7 mmol) of the title compound as a white solid in a yield of 89.0% (on the basis of pentaerythritol trimethacrylate)

[Spectral Data of the Title Compound]

$^1$H-NMR (CDCl$_3$) δ: 1.65–1.88 (m, 12H), 1.94 (br, s, 9H), 2.01 (m, 3H), 4.19 (s, 2H), 4.27 (s, 6H), 5.61 (br, s, 3H), 6.10 (br, s, 3H).

Example 6

[Production of Trimethylolpropane Dimethacrylate mono(1-Adamantanecarboxylate)]

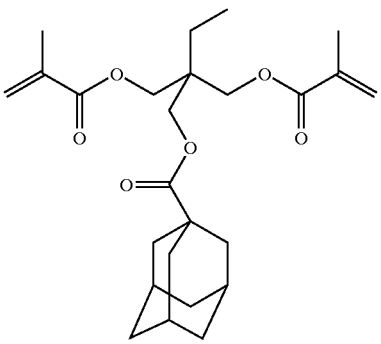

In a 500-ml round bottom flask equipped with a stirrer, thermometer, dropping funnel, cooling tube and calcium chloride tube, 45.0 g (166.5 mmol) of trimethylolpropane dimethacrylate, 19.75 g (249.7 mmol) of pyridine, 50 mg (0.40 mmol) of methoxyphenol, and 180 ml of toluene were placed, and 115 ml of a toluene solution of 36.38 g (183.1 mmol) of 1-adamantanecarboxylic chloride was added to the mixture at room temperature over 30 minutes with stirring. Next, the resulting mixture was heated to 100° C. and was stirred for 3 hours, was then cooled to room temperature, was successively washed with an aqueous saturated sodium carbonate solution (200 ml×2) and an aqueous saturated sodium chloride solution (200 ml×1) and was then dried over an appropriate amount of sodium sulfate. After removing the desiccating agent by filtration and the solvent by distillation under a reduced pressure, the resulting concentrate was purified by column chromatography on a silica gel (ethyl acetate/hexane=10/1) to thereby yield 61.42 g (142.0 mmol) of the title compound as a white solid in a yield of 85.3% (on the basis of trimethylolpropane dimethacrylate).

[Spectral Data of the Title Compound]

$^1$H-NMR (CDCl$_3$) δ: 0.94 (t, J=7.5 Hz, 3H), 1.56 (q, J=7.5 Hz, 2H), 1.65–1.90 (m, 12H), 1.94 (br, s, 6H), 2.01 (m, 3H), 4.05 (s, 2H), 4.14 (s, 4H), 5.58 (br, s, 2H), 6.10 (br, s, 2H).

What is claimed is:

1. An adamantane derivative represented by the following Formula (1), (6) or (9):

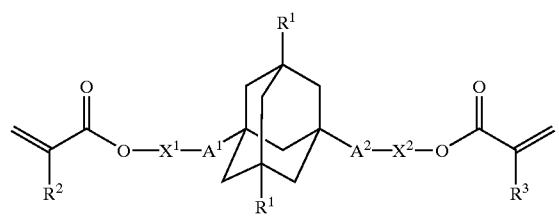

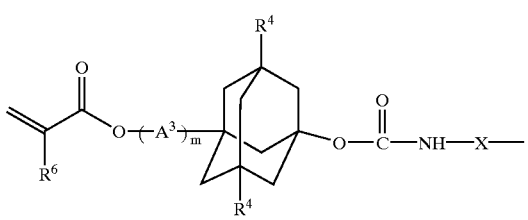

-continued

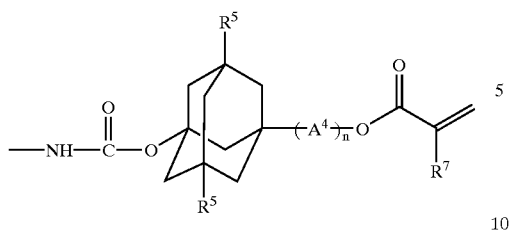

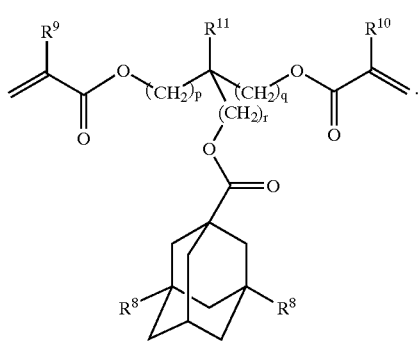

[wherein, in Formula (1), $R^1$ is a hydrogen atom or a methyl group; each of $R^2$ and $R^3$ is, identical to or different from each other, a hydrogen atom or a methyl group; each of $A^1$ and $A^2$ is, identical to or different from each other, a —C(=O)—O— group or —O—C(=O)— group, where the right-hand sides of these two integer from 1 to 6); and each of p, q and r denotes an integer from 1 to 6.]

2. A process for producing an adamantane derivative, said process comprising the step of allowing an adamantanedicarboxylic acid represented by the following Formula (2) or a reactive derivative thereof:

(2)

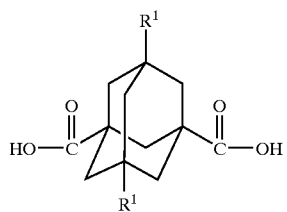

(wherein $R^1$ is a hydrogen atom or a methyl group) to react with (meth)acrylic hydroxyalkyl esters represented by the following Formulae (3a) and (3b):

(3a)

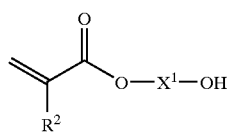

-continued (3b)

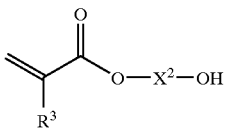

(wherein each of $R^2$ and $R^3$ is, identical to or different from each other, a hydrogen atom or a methyl group; and each of $X^1$ and $X^2$ is, identical to or different from each other, a straight- or branched-chain alkylene group having from 1 to 12 carbon atoms) to thereby yield an adamantane derivative represented by the following Formula (1a):

(1a)

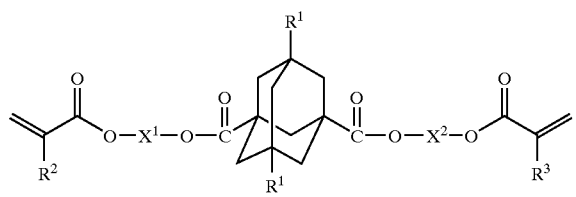

(wherein $R^1$, $R^2$, $R^3$, $X^1$ and $X^2$ have the same meanings as defined above.)

3. A process for producing an adamantane derivative, said process comprising the step of allowing an adamantanediol represented by the following Formula (4):

(4)

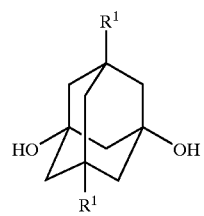

(wherein $R^1$ is a hydrogen atom or a methyl group) to react with (meth) acryloyloxy-group-containing carboxylic acids represented by the following Formulae (5a) and (5b) or reactive derivatives thereof:

(5a)

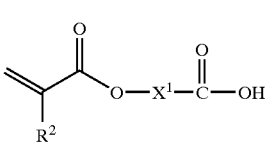

(5b)

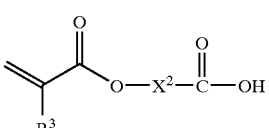

(wherein each of $R^2$ and $R^3$ is, identical to or different from each other, a hydrogen atom or a methyl group; and each of $X^1$ and $X^2$ is, identical to or different from each other, a straight- or branched-chain alkylene group having from 1 to 12 carbon atoms) to thereby yield an adamantane derivative represented by the following Formula (1b):

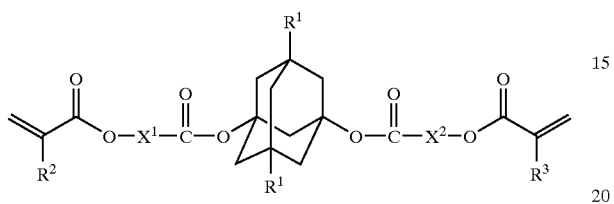

(1b)

(wherein $R^1$, $R^2$, $R^3$, $X^1$ and $X^2$ have the same meanings as defined above.)

4. A process for producing an adamantane derivative, said process comprising the step of allowing adamantanol derivatives represented by the following Formulae (7a) and (7b):

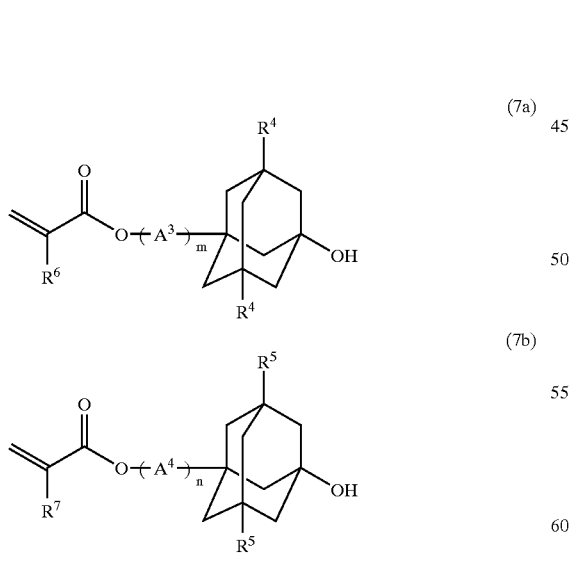

(7a)

(7b)

[wherein each of $R^4$ and $R^5$ is, identical to or different from each other, a hydrogen atom or a methyl group; each of $R^6$ and $R^7$ is, identical to or different from each other, a hydrogen atom or a methyl group; each of $A^3$ and $A^4$ is, identical to or different from each other, a group represented by the following formula:

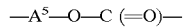

$-A^5-O-C(=O)-$ (wherein $A^5$ is a straight- or branched-chain alkylene group having from 1 to 6 carbon atoms, where the right-hand side of the above formula is on the adamantane ring side); and each of m and n independently denotes 0 or 1] to react with a diisocyanate compound represented by the following Formula (8):

OCN—X—NCO    (8)

(wherein X is a straight- or branched-chain alkylene group having from 1 to 12 carbon atoms)

to thereby yield an adamantane derivative represented by the following Formula (6):

(6)

(wherein $R^4$, $R^5$, $R^6$, $R^7$, $A^3$, $A^4$, X, m and n have the same meanings as defined above.)

5. A process for producing an adamantane derivative, said process comprising the step of allowing an adamantanecarboxylic acid represented by the following Formula (11) or a reactive derivative thereof:

(11)

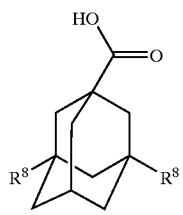

(wherein $R^8$ is a hydrogen atom or a methyl group) to react with a compound represented by the following Formula (12):

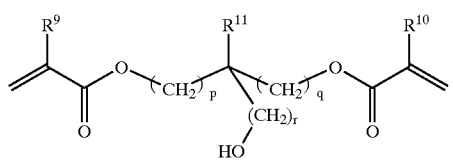 (12)

[wherein each of $R^9$ and $R^{10}$ is, identical to or different from each other, a hydrogen atom or a methyl group; $R^{11}$ is a hydrogen atom, a straight- or branched-chain alkyl group having from 1 to 4 carbon atoms, or a group represented by the following Formula (10):

 (10)

(wherein $R^{12}$ is an acryloyl group, a methacryloyl group, an 1-adamantylcarbonyl group, or a 3,5-dimethyladamant-1-ylcarbonyl group; and s denotes an integer from 1 to 6); and each of p, q and r independently denotes an integer from 1 to 6]

to thereby yield an adamantane derivative represented by the following Formula (9):

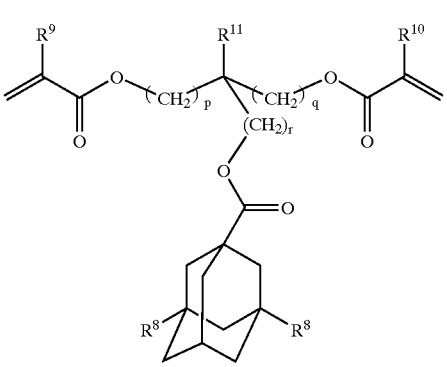 (9)

(wherein $R^8$, $R^9$, $R^{10}$, $R^{11}$, p, q and r have the same meanings as defined above.)

* * * * *